(12) United States Patent
Winder (10) Patent No.: US 6,585,647 B1
(45) Date of Patent: Jul. 1, 2003

(54) METHOD AND MEANS FOR SYNTHETIC STRUCTURAL IMAGING AND VOLUME ESTIMATION OF BIOLOGICAL TISSUE ORGANS

(76) Inventor: Alan A. Winder, 56 Patrick Rd., Westport, CT (US) 06880

(*) Notice: Subject to any disclaimer, the term of this patent is extended or adjusted under 35 U.S.C. 154(b) by 0 days.

(21) Appl. No.: 09/744,136
(22) PCT Filed: Jul. 21, 1999
(86) PCT No.: PCT/US99/16472
§ 371 (c)(1),
(2), (4) Date: Apr. 16, 2001
(87) PCT Pub. No.: WO00/04831
PCT Pub. Date: Feb. 3, 2000

Related U.S. Application Data
(60) Provisional application No. 60/093,518, filed on Jul. 21, 1998.

(51) Int. Cl.$^7$ ................................................ A61B 8/00
(52) U.S. Cl. .................... 600/437; 600/443; 128/916
(58) Field of Search ................ 600/437, 440–447, 600/448–457; 73/625, 626; 324/6.12; 348/384.1; 128/916

(56) References Cited

U.S. PATENT DOCUMENTS

| | | |
|---|---|---|
| 3,134,451 A | 5/1964 | Hanssen |
| 3,193,034 A | 7/1965 | Hutchinson et al. |
| 3,310,049 A | 3/1967 | Clynes |
| 3,433,663 A | 3/1969 | Underwood |
| 3,499,437 A | 3/1970 | Balamuth |
| 3,550,586 A | 12/1970 | Balamuth |
| 3,594,993 A | 7/1971 | Heyse |
| 3,701,352 A | 10/1972 | Bosworth |
| 3,760,799 A | 9/1973 | Crowson |
| 3,767,195 A | 10/1973 | Dimick |
| 3,828,769 A | 8/1974 | Mettler |
| 3,855,638 A | 12/1974 | Pilliar |
| 3,961,380 A | 6/1976 | Garr |
| 3,986,212 A | 10/1976 | Sauer |
| 4,105,017 A | 8/1978 | Ryaby et al. |
| 4,127,125 A | 11/1978 | Takemoto et al. |

(List continued on next page.)

FOREIGN PATENT DOCUMENTS

| | | |
|---|---|---|
| AU | 19950292 | 2/2000 |

(List continued on next page.)

OTHER PUBLICATIONS

Cass, "Fabrication of Continuous Ceramic Fiber by the Viscous Suspension Spinning Process," *Ceramic Bulletin*, vol. 70, No. 3, pp. 424–429 (1991).

Clarke, P.R. et al., "Physical and Chemical Aspects of Ultrasonic Disruption of Cells", *JASA* (1969), 47(2): 649–653.

(List continued on next page.)

*Primary Examiner*—Marvin M. Lateef
*Assistant Examiner*—Ali M. Imam
(74) *Attorney, Agent, or Firm*—Carter, DeLuca, Farrell & Schmidt, LLP (57) ABSTRACT

A system (10) having a processor, a memory, generates low frequency ultrasound signals to be applied to tissue (14) to generate a weighted sum of tissue ramp, step, and impulse signatures. The system (10) analyzes the tissue signatures to determine the low frequency target profile which is used to generate a graphic representation of the tissue as well as to estimate the volume of the tissue; to classify the tissue (14) as to type, and condition of the tissue using a set of stored tissue data. The classifier may include a neural network (34), and/or a nearest neighbor rule processor (36). The system (10) performs as a non-invasive acoustic measurement, an imaging system, and method which uses Synthetic Structural Imaging (SSI) techniques to provide unique information concerning the size, shape of biological structures for classification, visualization of normal, abnormal tissues, organs, biological structures, etc.

28 Claims, 3 Drawing Sheets

U.S. PATENT DOCUMENTS

| | | |
|---|---|---|
| 4,164,794 A | 8/1979 | Spector et al. |
| 4,170,045 A | 10/1979 | Estes |
| 4,176,664 A | 12/1979 | Talish |
| 4,206,516 A | 6/1980 | Pilliar |
| 4,216,766 A | 8/1980 | Duykers et al. |
| 4,227,111 A | 10/1980 | Cross et al. |
| 4,233,477 A | 11/1980 | Rice et al. |
| 4,269,797 A | 5/1981 | Mikiya et al. |
| 4,296,753 A | 10/1981 | Goudin |
| 4,312,536 A | 1/1982 | Lloyd |
| 4,315,503 A | 2/1982 | Ryaby et al. |
| 4,351,069 A | 9/1982 | Ballintyn et al. |
| 4,355,428 A | 10/1982 | Deloison et al. |
| 4,358,105 A | 11/1982 | Sweeney, Jr. |
| 4,361,154 A | 11/1982 | Pratt, Jr. |
| 4,365,359 A | 12/1982 | Raab |
| 4,383,533 A | 5/1983 | Bhagat et al. |
| 4,421,119 A | 12/1983 | Pratt, Jr. |
| 4,440,025 A | 4/1984 | Hayakawa et al. |
| 4,441,486 A | 4/1984 | Pounds |
| 4,446,586 A | 5/1984 | Reed et al. |
| 4,452,326 A | 6/1984 | Hanssen et al. |
| 4,476,847 A | 10/1984 | Dunn |
| 4,476,874 A * | 10/1984 | Taenzer et al. ............. 600/441 |
| 4,511,921 A | 4/1985 | Harlan et al. |
| 4,530,360 A | 7/1985 | Duarte |
| 4,536,894 A | 8/1985 | Galante et al. |
| 4,542,539 A | 9/1985 | Rowe, Jr. et al. |
| 4,542,744 A | 9/1985 | Barnes et al. |
| 4,550,714 A | 11/1985 | Talish |
| 4,556,066 A | 12/1985 | Semrow |
| 4,570,640 A | 2/1986 | Barsa |
| 4,573,996 A | 3/1986 | Kwiatek et al. |
| 4,594,662 A | 6/1986 | Devaney |
| 4,612,160 A | 9/1986 | Donlevy et al. |
| 4,627,429 A | 12/1986 | Tsuk |
| 4,630,323 A | 12/1986 | Sage et al. |
| 4,644,942 A | 2/1987 | Sump |
| 4,677,438 A | 6/1987 | Michiguchi et al. |
| 4,687,195 A | 8/1987 | Potts |
| 4,708,127 A | 11/1987 | Abdelghani |
| 4,710,655 A | 12/1987 | Masaki |
| 4,726,099 A | 2/1988 | Card |
| 4,763,661 A | 8/1988 | Sommer et al. |
| 4,770,184 A | 9/1988 | Greene, Jr. et al. |
| 4,774,959 A | 10/1988 | Palmer et al. |
| RE32,782 E | 11/1988 | Pratt, Jr. |
| 4,782,822 A | 11/1988 | Ricken |
| 4,787,070 A | 11/1988 | Suzuki et al. |
| 4,787,888 A | 11/1988 | Fox |
| 4,792,336 A | 12/1988 | Hlavacek et al. |
| 4,802,477 A | 2/1989 | Gabbay |
| 4,830,015 A | 5/1989 | Okazaki |
| 4,836,316 A | 6/1989 | Carnevale et al. |
| 4,855,911 A | 8/1989 | Lele et al. |
| 4,858,599 A | 8/1989 | Halpern |
| 4,867,169 A | 9/1989 | Machida et al. |
| 4,891,849 A | 1/1990 | Robinson |
| 4,905,671 A | 3/1990 | Senge et al. |
| 4,913,157 A | 4/1990 | Pratt, Jr. et al. |
| 4,917,092 A | 4/1990 | Todd et al. |
| 4,926,870 A | 5/1990 | Brandenburger |
| 4,932,951 A | 6/1990 | Liboff et al. |
| 4,933,230 A | 6/1990 | Card et al. |
| 4,936,303 A | 6/1990 | Detwiler et al. |
| 4,941,474 A | 7/1990 | Pratt, Jr. |
| 4,947,853 A | 8/1990 | Hon |
| 4,979,501 A | 12/1990 | Valchanov et al. |
| 4,982,730 A | 1/1991 | Lewis, Jr. |
| 4,986,275 A | 1/1991 | Ishida et al. |
| 4,993,413 A | 2/1991 | McLeod et al. |
| 4,995,883 A | 2/1991 | Demane et al. |
| 5,000,183 A | 3/1991 | Bonnefous |
| 5,000,442 A | 3/1991 | Dalebout et al. |
| 5,003,965 A | 4/1991 | Talish et al. |
| 5,004,476 A | 4/1991 | Cook |
| 5,016,641 A | 5/1991 | Schwartz |
| 5,018,285 A | 5/1991 | Zolman et al. |
| 5,046,484 A | 9/1991 | Bassett et al. |
| 5,054,490 A | 10/1991 | Rossman et al. |
| 5,067,940 A | 11/1991 | Liboff et al. |
| 5,080,672 A | 1/1992 | Bellis |
| 5,088,976 A | 2/1992 | Liboff et al. |
| 5,099,702 A | 3/1992 | French |
| 5,100,373 A | 3/1992 | Liboff et al. |
| 5,103,806 A | 4/1992 | McLeod et al. |
| 5,106,361 A | 4/1992 | Liboff et al. |
| 5,107,853 A | 4/1992 | Plyter |
| 5,108,452 A | 4/1992 | Fallin |
| 5,133,420 A | 7/1992 | Smith |
| 5,134,999 A | 8/1992 | Osipov |
| 5,139,498 A | 8/1992 | Astudillo Ley |
| 5,140,988 A | 8/1992 | Stouffer et al. |
| 5,143,069 A | 9/1992 | Kwon et al. |
| 5,143,073 A | 9/1992 | Dory |
| 5,163,598 A | 11/1992 | Peters et al. |
| 5,172,692 A | 12/1992 | Kulow et al. |
| 5,178,134 A | 1/1993 | Vago |
| 5,181,512 A | 1/1993 | Viebach et al. |
| 5,184,605 A | 2/1993 | Grzeszykowski |
| 5,186,162 A | 2/1993 | Talish et al. |
| 5,191,880 A | 3/1993 | McLeod et al. |
| 5,197,475 A | 3/1993 | Antich et al. |
| 5,201,766 A | 4/1993 | Georgette |
| 5,209,221 A | 5/1993 | Riedlinger |
| 5,211,160 A | 5/1993 | Talish et al. |
| 5,230,334 A | 7/1993 | Klopotek |
| 5,230,345 A | 7/1993 | Curran et al. |
| 5,230,921 A | 7/1993 | Waltonen et al. |
| 5,235,981 A | 8/1993 | Hascoet et al. |
| 5,254,123 A | 10/1993 | Bushéy |
| 5,259,384 A | 11/1993 | Kaufman et al. |
| 5,269,306 A | 12/1993 | Warnking et al. |
| 5,273,028 A | 12/1993 | McLeod et al. |
| 5,284,143 A | 2/1994 | Rattner |
| 5,285,788 A | 2/1994 | Arenson et al. |
| 5,295,931 A | 3/1994 | Dreibelbis et al. |
| 5,301,683 A | 4/1994 | Durkan |
| 5,307,284 A * | 4/1994 | Brunfeldt et al. ........ 324/76.12 |
| 5,309,898 A | 5/1994 | Kaufman et al. |
| 5,310,408 A | 5/1994 | Schryver et al. |
| 5,314,401 A | 5/1994 | Tepper |
| 5,316,000 A | 5/1994 | Chapelon et al. |
| 5,318,561 A | 6/1994 | McLeod et al. |
| 5,318,779 A | 6/1994 | Hakamatsuka et al. |
| 5,322,067 A | 6/1994 | Prater et al. |
| 5,323,769 A | 6/1994 | Bommannan et al. |
| 5,327,890 A | 7/1994 | Matura et al. |
| 5,330,481 A | 7/1994 | Hood et al. |
| 5,330,489 A | 7/1994 | Green et al. |
| 5,334,214 A | 8/1994 | Putnam |
| 5,339,804 A | 8/1994 | Kemp |
| 5,340,510 A | 8/1994 | Bowen |
| 5,351,389 A | 10/1994 | Erickson et al. |
| 5,363,850 A | 11/1994 | Soni et al. |
| 5,366,465 A | 11/1994 | Mirza |
| 5,367,500 A | 11/1994 | Ng |
| 5,376,065 A | 12/1994 | McLeod et al. |
| 5,380,269 A | 1/1995 | Urso |

| | | |
|---|---|---|
| 5,386,830 A | 2/1995 | Powers et al. |
| 5,393,296 A | 2/1995 | Rattner |
| 5,394,878 A | 3/1995 | Frazin et al. |
| 5,398,290 A | 3/1995 | Brethour |
| 5,400,795 A | 3/1995 | Murphy et al. |
| 5,405,389 A | 4/1995 | Conta et al. |
| 5,409,446 A | 4/1995 | Rattner |
| RE34,959 E | 5/1995 | Potts |
| 5,413,550 A | 5/1995 | Castel |
| 5,415,167 A | 5/1995 | Wilk |
| 5,417,215 A | 5/1995 | Evans et al. |
| 5,424,550 A | 6/1995 | Kawano et al. |
| 5,431,612 A | 7/1995 | Holden |
| 5,434,827 A | 7/1995 | Bolorforosh |
| 5,441,051 A | 8/1995 | Hileman et al. |
| 5,441,058 A | 8/1995 | Fareed |
| 5,448,994 A | 9/1995 | Iinuma |
| 5,460,595 A | 10/1995 | Hall et al. |
| 5,466,215 A | 11/1995 | Lair et al. |
| 5,468,220 A | 11/1995 | Sucher |
| 5,476,438 A | 12/1995 | Edrich et al. |
| 5,478,306 A | 12/1995 | Stoner |
| 5,492,525 A | 2/1996 | Gibney |
| 5,495,846 A | 3/1996 | Uehara et al. |
| 5,496,256 A | 3/1996 | Bock et al. |
| 5,501,657 A | 3/1996 | Feero |
| 5,507,800 A | 4/1996 | Strickland |
| 5,507,830 A | 4/1996 | DeMane et al. |
| 5,509,933 A | 4/1996 | Davidson et al. |
| 5,520,612 A | 5/1996 | Winder et al. |
| 5,524,624 A | 6/1996 | Tepper et al. |
| 5,526,815 A | 6/1996 | Granz et al. |
| 5,541,489 A | 7/1996 | Dunstan |
| 5,547,459 A | 8/1996 | Kaufman et al. |
| 5,556,372 A | 9/1996 | Talish et al. |
| 5,578,060 A | 11/1996 | Pohl et al. |
| 5,615,466 A | 4/1997 | Safari et al. |
| 5,626,554 A | 5/1997 | Ryaby et al. |
| 5,626,630 A | 5/1997 | Markowitz et al. |
| 5,630,837 A | 5/1997 | Crowley |
| 5,648,941 A | 7/1997 | King |
| 5,656,016 A | 8/1997 | Ogden |
| 5,680,863 A | 10/1997 | Hossack et al. |
| 5,690,608 A | 11/1997 | Watanabe et al. |
| 5,691,960 A | 11/1997 | Gentilman et al. |
| 5,699,803 A | 12/1997 | Carodiskey |
| 5,702,353 A | 12/1997 | Guzzini et al. |
| 5,706,818 A | 1/1998 | Gondo |
| 5,708,236 A | 1/1998 | Shaanan et al. |
| 5,721,400 A | 2/1998 | Haraldsson et al. |
| 5,725,482 A | 3/1998 | Bishop |
| 5,730,705 A | 3/1998 | Talish et al. |
| 5,738,625 A | 4/1998 | Gluck |
| 5,741,317 A | 4/1998 | Ostrow |
| 5,743,862 A | 4/1998 | Izumi |
| 5,755,746 A | 5/1998 | Lifshey et al. |
| 5,762,616 A | 6/1998 | Talish |
| 5,779,600 A | 7/1998 | Pape |
| 5,785,656 A | 7/1998 | Chiabrera et al. |
| 5,818,149 A | 10/1998 | Safari et al. |
| 5,829,437 A | 11/1998 | Bridges |
| 5,868,649 A | 2/1999 | Erickson et al. |
| 5,871,446 A | 2/1999 | Wilk |
| 5,886,302 A | 3/1999 | Germanton et al. |
| 5,899,425 A | 5/1999 | Corey, Jr. et al. |
| 5,904,659 A | 5/1999 | Duarte et al. |
| 5,957,814 A | 9/1999 | Eschenbach |
| 5,997,490 A | 12/1999 | McLeod et al. |
| 6,019,710 A | 2/2000 | Dalebout et al. |
| 6,022,349 A | 2/2000 | McLeod et al. |
| 6,068,596 A | 5/2000 | Weth et al. |

| | | |
|---|---|---|
| 6,080,088 A | 6/2000 | Petersen et al. |
| 6,086,078 A | 7/2000 | Ferez |
| 6,093,135 A | 7/2000 | Huang |
| 6,165,144 A | 12/2000 | Talish et al. |
| 6,179,797 B1 | 1/2001 | Brotz |
| 6,206,843 B1 | 3/2001 | Iger et al. |
| 6,213,958 B1 | 4/2001 | Winder |
| 6,261,221 B1 | 7/2001 | Tepper et al. |
| 6,261,249 B1 | 7/2001 | Talish et al. |
| 6,273,864 B1 | 8/2001 | Duarte |
| 6,360,027 B1 * | 3/2002 | Hossack et al. ......... 348/384.1 |

FOREIGN PATENT DOCUMENTS

| | | |
|---|---|---|
| CA | 1328485 | 4/1994 |
| DE | 3639263 A1 | 6/1987 |
| DE | 3639263 A1 | 6/1987 |
| DE | 19613425 A1 | 1/1997 |
| DE | 19613425 | 1/1997 |
| EP | 0 181 506 A2 | 5/1986 |
| EP | 331 348 A1 | 9/1989 |
| EP | 0 536 875 A1 | 4/1993 |
| EP | 0 679 371 A1 | 11/1995 |
| EP | 0 695 559 | 2/1996 |
| GB | 2156983 A | 10/1985 |
| GB | 2277448 A | 11/1994 |
| GB | 2 303 552 A | 2/1997 |
| JP | SHO 62-47359 | 3/1987 |
| JP | HEI4-82567 | 3/1992 |
| JP | HEI 4-82568 | 3/1992 |
| JP | HEI 4-82569 | 3/1992 |
| JP | 4082567 | 3/1992 |
| JP | 4082568 | 3/1992 |
| JP | HEI 41992-82567 | 3/1992 |
| JP | HEI 5-269159 | 10/1993 |
| WO | WO 85/03449 | 8/1985 |
| WO | WO 88/00845 | 2/1988 |
| WO | WO 88/02250 | 4/1988 |
| WO | WO 90/06720 | 6/1990 |
| WO | WO 94/13411 | 6/1994 |
| WO | WO 95/03744 | 2/1995 |
| WO | WO 95/33416 | 12/1995 |
| WO | WO 96/25112 | 8/1996 |
| WO | WO 96/25888 | 8/1996 |
| WO | WO 97/33649 | 9/1997 |
| WO | WO 98/10729 | 3/1998 |
| WO | WO 98/34578 | 8/1998 |
| WO | WO 98/47570 | 10/1998 |
| WO | WO 99/18876 | 4/1999 |
| WO | WO 99/22652 | 5/1999 |
| WO | WO 99/48621 | 9/1999 |
| WO | WO 99/56829 | 11/1999 |
| WO | WO 00/03663 | 1/2000 |
| WO | WO 00/28925 | 5/2000 |
| WO | WO 00/71207 | 11/2000 |
| WO | WO 00/76406 | 12/2000 |

OTHER PUBLICATIONS

Hill, C.R., "Ultrasonic Exposure Thresholds for Changes in Cells and Tissues", *JASA* (1972), 52(2): 667–672.

McLeod, et al., "Improved Postural Stability Following Short Term Exposure to Low Level Whole Body Vibration," $44^{th}$ Annual Meeting, Orthopaedic Research Society, Mar. 16–19, 1998, New Orleans, Louisiana, p. 89–15.

Phoenix (Business Wire), Jul. 8, 1997 via CompanyLink—OrthoLogic Corp.

Pilgrim, et al., "An Extension of the Composite Nomenclature Scheme," Med. Res. Bull., vol. 22, pp. 877–894 (1987).

"Reflex Sympathetic Dystrophy, Does RSD Exist?" www.arbon.com (Jun. 4, 1997).

"Reflex Sympathetic Dystrophy: The Pain That Doesn't Stop," tcc.cc.nc.us (Jun. 4, 1997).

RSDnet.org "Reflex Sympathetic Dystrophy," www.rsdnet.org (Jun. 4, 1997).

RSDnet.org "Reflex Sympathetic Dystrophy," www.rsdnet.org (Jun. 4, 1997).

Tavakoli and Evans, "The Effect of Bone Structure on Ultrasonic Attenuation and Velocity," Ultrasonics, vol. 30, No. 6 (1992).

Abstract, (Proceedings of the 11th Int'l. Conference on Medical and Biological Engineering) "Ultrasonic Stimulation of Fracture Healing", 1976.

Abstract, (Proceedings of the III Congress on Biomedical Engineering) "Ultrasonic Action on Callus Formation in Bones", 1975.

Abstract, (Proceedings of the IV Brazilain Congress on Biomedical Engineering) "Ultrasound in the Treatment of Fractures", 1977.

ASTM Designation: D790M–93 Metric, "Standard Test Methods for flexural Properties of Unreinforced and Reinforced Plastics and Electrical Insulating Materials [Metric]", pp. 176–184, (Dec. 1993).

ASTM Designation: C1161–90, "Standard Test Method for Flexural Strength of Advanced Ceramics at Ambient Temperature," pp. 324–330.(Feb. 1991).

Brochure: "The Science Behind the Technology," distributed by Smith & Nephew for EXOGEN. (no date).

Arai et al., "The Effect of Ultrasound Stimulation on Disuse Osteoporosis", BRAGS 17, 1993.

Berridge, M.J., "Inositol Trisphosphate and Calcium Signaling", Nature (1993), 361: 315–325.

Duarte, L.R., "The Stimulation of Bone Growth by Ultrasound", Arch. Orthop. Trauma Surg (1983), 101: 153–159.

Dyson, M., "Therapeutic Applications of Ultrasound", Biological Effects of Ultrasound (1985), Nyborg, W.L. and Ziskin, M.C., eds; Churchill Livingstone Inc., New York, Chapter 11.

Goodship, A.E. et al., "The Influence of Induced Micromovement Upon the Healing of Experimental Tibial Fractures", J. Bone and Joint Surg. (1985), 67–B(4): 650–655.

Heckman, J.D. et al., "Acceleration of Tibial Fracture Healing by Non–Invasive Low–Intensity Pulsed Ultrasound", J. Bone and Joint Surg. (1994), 76–A(1): 26–34.

Howkins, S.D., "Diffusion Rates and the Effect of Ultrasound", Ultrasonics (1969), 129–130.

Kristiansen, T.K. et al., "Accerlated Healing of Distal Radial Fractures with the Use of Specific, Low–Intensity Ultrasound", J. Bone and Joint Surg. (1997), 79–A(7) 961–973.

Maurice Hilario, "Low–Intensity Ultrasound Radiation in the Tissue Repair of Trophic Leg Ulcers", 1983, University of Sao Paulo, pp. 1–125.

Pethica, B.A., et al., Abstract, Biological Repair and Growth Society, Jun. 1998.

Pilla, A.A. et al., "Non–Invasive Low–Intensity Ultrasound Accelerates Bone Repair: Rabbit Fiubla Model and Human Colles' and Tibial Fractures", Annual Intl. Conference of IEEE–EMBS Proceedings (1990), 12:1573–1574.

Ter Haar, G., et al., "Basic Physics of Therapeutic Ultrasound", Physiotherapy (1987), 73(3): 110–113.

Wallace, A.L.; Draper E.R.C.; Strachan, R.K.; McCarthy, I.D.; Hughes, S.P.F., "The Vascular Response to Fracture Micromovement", Clinical Orthopaedics and Related Research (1994), 301: 281–290.

Wang, S.J. et al., "Low–Intensity Ultrasound Treatment Increases Strength in a Rat Femoral Fracture Model", J. Ortho Research (1994), 12: 40–47.

Webster, D.F.et al., "The Role of Ultrasound–Induced Cavitation in the 'In Vitro' Stimulation of Collagen Synthesis in Human Fibroblasts", Ultrasonics (1980), 33–37.

Yang, K.H. et al., "Exposure to Low–Intensity Ultrasound Treatment Increases Aggrecan Gene Expression in a Rat Femur Fracture Model", J. Ortho Research (1996), 14:802–809.

Treatment of Osteochondral Defects in Rabbits with SAFHS—Parts I and II, EX1095–01R, EX1096–01R.

Treatment of Osteochondral Defects in Rabbits with SAFHS—Part III, EX1097–01R (Aug. 26, 1997).

Cook, Stephen and L. Patron, "Treatment of Osteorchondral Defects in Rabbits with SAFHS—A Mosaicplasty Model"—Final Report, EX1098–04R (Aug. 12, 1999).

Acoustic Emission—An Update, by Arthur E. Lord, Jr., 1981, Physical Acoustics, vol. XV, pp. 295–360.

Acoustic Emission and Diagnosis of Osteoporosis, by S. Hanagud, G. T. Hannon and R. Clinton, 1974, Ultrasonic Symposium Proceedings (IEEE), pp. 77–81.

Acoustic Emission in Bone Substance, by S. Hanagud, R.G. Clinton and J.P. Lopez, 1973, Biomechanics Symposium Proceedings (ASME), pp. 79–81.

Acoustic Emission Inspection, by Adrian A. Pollock, 1992, ASM Handbook, vol. 17, Nondestructive Evaluation and Quality Control, pp. 278–293.

Acoustic Emission Techniques in the Development of a Diagnostic Tool for Osteoporosis, by S. Hanagud and R. G. Clinton, 1975, Ultrasonic Symposium Proceedings (IEEE), pp. 41–45.

Application of an intelligent signal processing system to acoustic emission analysis, by Igo Grabec and Wolfgang Sachse, Mar. 1989, Acoustic Society of America, pp. 787–791.

Application of correlation techniques for localization of acoustic emission sources, by I. Grabec, 1978, IPC Business Press Ltd., pp. 111–115.

Cornejo, et al., "Large–Area Flexible–Array Piezoelectric Ceramic/Polymer composite Transducer for Bone Healing Acceleration," presented by ISAFXI, Montreux, Switzerland (1998).

Clough, R. and J. Simmons, "Theory of Acoustic Emission," Metallurgy Division, national Bureau of Standards. (no date).

Fritton, et al., "Whole–Body Vibration in the Skeleton: Development of a Resonance–Based Testing Device," Annals of Biomedical Engineering, vol. 25, pp. 831–839 (1997).

Goodship, et al., "Low magnitude high frequency mechanical stimulation of endochondral bone repair" 43rd Annual Meeting Orthopeadic Research Society, vol. 22, Sec. 1, Feb. 9–13 (1997).

J. Kenwright, et al., "Controlled Mechanical Stimulation in the Treatment of Fibial Fractures," Orthopedics, Clinical Orthopedics and Related Research (1989) 241:36–47.

Jankovich, "The Effects of Mechanical Vibration on Bone Development in the Rat," J. Biomechanics, 1972, vol. 5, pp. 241–250.

Ko, "Preform Fiber Architecture for Ceramic–Matrix Composites," Ceramic Bulletin, vol. 68, No. 2, pp. 401–414(1989).

Newnham, et al., Connectivity and Piezoelectric–Pyroelectric Composites, Med. Res. Bull., vol. 13, pp. 525–536 (1978).

Pauer, "Flexible Piezoelectric Material," pp. 1–5, (no date).

Powell, et al., "A Performance Appraisal of Flexible Array Structures Using a Facet Ensemble Scattering Technique," *1991 Ultrasonic Symposium,* pp. 753–766.

Powell, et al., Flexible Ultrasonic Transducer Arrays for Nondestructive Evaluation Applications—Part I: The Theoretical Modeling Approach, "*IEEE Transactions on Ultrasonics, Ferroelectrics, and Frequency Control,* "vol. 43, No. 3, May 1996, pp. 385–392.

Powell, et al., "Flexible Ultrasonic Transducer Arrays for Nondestructive Evaluation Applications—Part II: Performance Assessment of different Array Configurations," *IEEE Transactions on Ultrasonics, Ferroelectrics, and Frequency Control,* vol. 43, No. 3, May 1996, pp. 393–402.

Sarvazyan, "Some General Problems of Biological Action of Ultrasound," IEEE Transactions on Sonics and Ultrasonics, vol. 30, No. 1, Jan. 1983.

Ultrasound as a Tool for Investigating Bone: Fundamental Principles and Perspectives for Use in Osteoporosis, by J. G. Bloch, 1993, Expanson Scientifique Francaise.

Y. Qin, et al., "Correlation of In Vivo Bone Adaptation and Mechanical Parameters Using Low Magnitude, High Frequency Loading," $41^{st}$ Annual Meeting Orthopaedic Research Soc., vol. 20—Sec. 1, Feb. 13–16 (1955).

Bascom, "Other Continuous Fibers," 118/Constitutent Material Form.

Bascom, "Other Discontinuous Forms," 120/Constituent Material Forms.

"Development of Flexible Pieoelectric Transducers and Matching Layers for EXOGEN Incorporated," Final Report, Covering Period Apr. 1, 1997–Feb. 28, 1998, Rutgers University.

Grewe, et al., "Acoustic Properties of Particle Polymer Composite for Ultrasonic Transducer Backing Applications," *IEEE,* (1990).

Grewe, Martha G., "Acoustic Matching And Backing Layer for Medical Ultrasonic Transducers," A Thesis in Solid State Science, The Pennsylvania State University; (May 1989), The Center for Ceramics Research, Rutgers.

Gururaja, T., "Piezoelectric Composite Materials for Ultrasonic Transducer Applications," A Thesis in Solid State Science, The Pennsylvania State University, May 1984.

Gururaja, "Piezoelectrics for Medical Ultrasonic Imaging," *Am. Ceram. Soc. Bull.,* vol. 73, No. 5, pp. 50–55 (May 1994).

Hall, et al., "The design and evaluation of ultrasonic arrays using 1–3 connectivity composites," *SPIE,* pp. 216–227, vol. 1733 (1992).

Pilla, et al., "Non–Invasive Low–Intensity Pulsed Ultrasound Accelerates Bone Healing in the Rabbit," *Journal of Orthopaedic Trauma,* vol. 4, No. 3, pp. 246–253 (1990).

Safari, "Development of piezoelectric composites for transducers," *J. Phys.France,* 4:1129–1149 (1994).

Selfridge, "Approximate Material Properties in Isotropic Materials," *IEEE Transactions on Sonics and Ultrasonics,* May 9, 1985).

Souquet, et al., "Design of Low–Loss Wide–Band Ultrasonic Transducers for Noninvasive Medical Application," *IEEE Transactions on Sonics and Ultrasonics,* pp. 75–81, vol. SU–26, No. 2, Mar. 1979.

Waller, et al., "Poling of Lead Zirconate Titanate Ceramics and Flexible Piezoelectric Composites by the Corona Discharge Technique," *J. Am. Ceram. Soc.,* 72(2):322–24 (1989).

Winder, Alan, "Synthetic Structural Imaging and Volume Estimation of Biological Tissue Organs," ,Acoustic Sciences Associates, Dec. 1995.

Winder, Alan, "Acoustic Emission Monitoring for the Detection, Localization and Classification of Metabolic Bone Disease," Acoustic Sciences Associates, Dec. 1995.

Wu and Cubberly, "Measurement of Velocity and Attenuation of Shear Waves in Bovine Compact Bone Using Ultrasonic Spectroscopy," Med. & Biol., vol. 23, No. 1,129–134, 1997.

Tavakoli and Evans , 1992 (no other information available at this time).

Pethica, B.A., et al., Abstract, Biological Repair and Growth Society, Jun. 1998.

Goodship, et al., "Low magnitude high frequency mechanical stimulation of endochondral bone repair" $43^{rd}$ Annual Meeting Orthopeadic Research Society, vol. 22, Sec. 1, Feb. 9–13 (1997).

Y. Qin, et al., "Correlation of In Vivo Bone Adaptation and Mechanical Parameters Using Low Magnitude, High Frequency Loading," $41^{st}$ Annual Meeting Orthopaedic Research Soc., vol. 20 –Sec. 1, Feb. 13–16 (1955).

Grewe, et al., "Acoustic Properties of Particle Polymer Composite for Ultrasonic Transducer Backing Applications," *IEEE,* (1990).

Wu and Cubberly, "Measurement of Velocity and Attenuation of Shear Waves in Bovine Compact Bone Using Ultrasonic Spectroscopy," Med. & Biol., vol. 23, No. 1, 129–134, 1997.

Pilla, et al., "Non–Invasive Low–Intensity Pulsed Ultrasound Accelerates Bone Healing in the Rabbit," *Journal of Orthopaedic Trauma,* vol. 4, No. 3, pp. 246–253 (1990).

Bascom, "Other Continuous Fibers," 118/Constituent Material Form.

Bascom, "Other Discontinuous Forms," 120/Constituent Material Forms.

Niemczewski, "A Comparison of ultrasonic cavitation intensity in liquids," *Ultrasonics,* 18(3): 107–110 (May 1980).

* cited by examiner

METHOD AND MEANS FOR SYNTHETIC STRUCTURAL IMAGING AND VOLUME ESTIMATION OF BIOLOGICAL TISSUE ORGANS

This application claims the benefit of provisional application 60/093,518 filed Jul. 21, 1998.

BACKGROUND

1. Technical Field

This disclosure relates to medical imaging, and in particular to a system and method for imaging and determining body organs.

2. Description of the Related Art

The noninvasive visualization of the internal anatomy of organ systems, and the supporting vascular network, provide invaluable medical diagnostic information of the patient. There have been considerable studies over the past ten years investigating volume visualization techniques for representing anatomical structures, using direct volume rendering and surface-fitting algorithms. These volume visualization techniques have been applied to various imaging modalities, such as ultrasound (US), magnetic resonance imaging (MRI), and computer tomography (CT).

In the field of diagnostic ultrasound, the use of conventional 2-D images requires the operator to try to mentally reconstruct and visualize the 3-D properties of the anatomy and related pathology. However, the ability to "think 3-D" varies considerably among clinicians and depends on their experience and innate ability in spatial perception. It is sometimes very difficult for the radiologist to develop a 3-D "picture" from the 2-D slices, to detect some lesions even with multiple views, and to visualize the supporting vascular system.

Three-dimensional ultrasound (3-D US) images are derived from two-dimensional contigous slices from conventional ultrasound scans. The tissue volume is spatially sampled, digitally stored and simultaneously displayed in a multiplanar array format to provide any three perpendicular anatomic planes desired, with rotation, thresholding and dissection (electronic scalpel), as needed, in order to optimally view the structures of interest. By maintaining the entire volume of data, analysis can be performed off-line, after the patient has left the clinic. This allows the multiplanar images to be reviewed in many arbitrary planes and with various processing options. For example, analysis can obtain specific region-of-interest statistics and their variation with time, merge information from multiple modalities, and allow for motion description and compensation.

3-D US imaging has been very effective in Ob/Gyn studies. It has been successfully used for detecting congenital abnormalities in fetal surface features (gestational ages 10 to 39 weeks), such as cleft lip and cleft palate, and for the early detection of chromosomal anomalies in the first trimester, distinguishing between cystic hygroma colli and physiologic nuchal translucency. 3D US has also permitted measurement of fetal organ volume for assessment of fetal growth and fetal abnormalities. For the first time, 3-D US permits the possibility of measuring the fetal lung volume and relating it to gestational age and fetal weight. 3-D multiplanar US can also be effective in identifying and assessing the standard cardiac planes from 14 weeks to term; clinical tests have shown that a 3-D measure of cardiac volume can be used to improve screening for fetal cardiac anomalies, with best results between 22 and 27 weeks gestation.

3-D US has also been effective in improving visualization of vessels and tumors in the prostate gland and breast, for visualizing the cardiac chambers, uterine anatomy, carotid artery and endoluminal structures. In recent clinical prostate studies, 3-D US gave a greater confidence level in identifying permanent transperineal radioactive seed implants, for the goal of real-time optimization of prostate brachytherapy. In breast studies, intraoperative and 3-D US are very effective in detecting and localizing areas of free silicone from ruptured breast implants when the ruptured implants are surgically removed. 3-D US gives a more accurate spatial localization of lesions for biopsy, compared to conventional 2-D US, and provides an accurate assessment of vascular structures and their related pathologies. In a broad range of clinical studies, 3-D endoluminal US provided unique information about spatial relationships of anatomic structures, such as the size and shape of the vascular lumen and the distribution, location and type of plaque, that could not be obtained with conventional 2-D imaging. 3-D US can present a more accurate distribution of tumor along the ureter, and its relationship adjacent structures, and provide a measure of the tumor volume. It can also greatly facilitate the visualization and staging of colorectal masses.

Some major limitations to 3-D ultrasound imaging are (1) the considerable number of "looks" or "slices" that are required for image reconstruction (typically several hundred slices in magnetic resonance imaging (MRI) and computed tomography (CT) and about 64 slices in ultrasound), (2) the long data acquisition time required for imaging, (3) the accuracy required for multi-plane anatomical registration (for example, resolutions less than about 0.5 mm), and (4) the requirements for large memory storage and rapid computation. There is a need for improved imaging technology to address such limitations; for example, a shortened acquisition time greatly minimizes the effects of target movement, such as fetal motion, and results in less exposure time with the accompanying less risk of bioeffects from normal biological activity or from sudden movements.

Other imaging techniques have been used for improved detection and classification of objects. For example, Synthetic Structural Imaging (SSI) techniques use low frequency transmissions for the successful detection and classification in both radar and sonar, of aircraft and of acoustic mines and submarines, respectively.

The SSI concept has been demonstrated to provide acoustical target identification and structural feature estimation in sonar applications. Test results have indicated that the acoustic transient response is uniquely characteristic of target identity, with features strongly related to simple geometrical shape features. It has been shown that such signatures may be used for a narrow bandwidth to provide pictorial information of sufficient quality as well as volume estimates of sufficient accuracy for substantially accurate target identification.

SSI employs ramp response analysis, which was developed in radar studies of airwing identification, and has also been successfully applied to imaging underwater (scaled) targets. Similar to conventional high frequency imaging, the SSI method is direction-dependent, but is considerably more robust. It has less resolution than conventional techniques but its correlation to shape is much stronger. SSI technology has been shown in previous experimental studies to be very promising for specific radar and sonar applications.

The application of SSI techniques to biological mediums may provide an estimate of the volume of biological organs, tumors and other structures. To date, there has been little progress in estimating the primary tissue classifiers of volume, size and shape in a clinical environment and relating them to tissue pathology. In addition, the discrimination of normal tissue from abnormal tissue has not been successfully accomplished using SSI.

SUMMARY

A novel, non-invasive, acoustic measurement and imaging system and method is disclosed which uses SSI techniques to provide unique information concerning the size and shape of biological tissue structures for classification and visualization of normal and abnormal tissues, organs, tumors, etc.

The SSI system includes a processor and memory for generating low frequency ultrasound signals to be applied to a biological structure to generate a synthetic structural image of the structure. The SSI system analyzes the low frequency ramp response of the tissue structure which is used to generate a graphic representation of the tissue structure as well as to estimate the volume of the tissue structure and to classify the tissue structure as to type and condition of the tissue using a set of stored tissue data. The classifier may include a neural network and/or a nearest neighbor rule processor.

The disclosed system and method utilize low frequency ultrasound transmissions for detection and classification, in which the amplitude and phase information as a function of tissue type, target direction and frequency are stored as an acoustic database. The system exploits a correlation between target shape and low frequency signature features.

Low frequency imaging in combination with high frequency imaging requires considerably fewer imaging planes or "slices" than conventional methods to realize real-time 3-D imaging of tissue structures. The system and method provide a unique measure of biological tissue volume as well as material composition, which may be used as inputs to a classifier for tissue classification. Predetermined tissue-specific signal waveforms, a priori information concerning the general properties and anatomical location of biological "targets" of interest, and temporal and frequency processing are used to minimize possible ambiguities and artifacts. The disclosed system and method may be integrated with existing high-end radiology or cardiology imaging systems, including the use of color flow imaging techniques.

BRIEF DESCRIPTION OF THE DRAWINGS

The features of the disclosed tissue imaging system and method will become more readily apparent and may be better understood by referring to the following detailed description of illustrative embodiments of the present invention, taken in conjunction with the accompanying drawings, in which.

DESCRIPTION OF THE PREFERRED EMBODIMENTS

Figure 1:
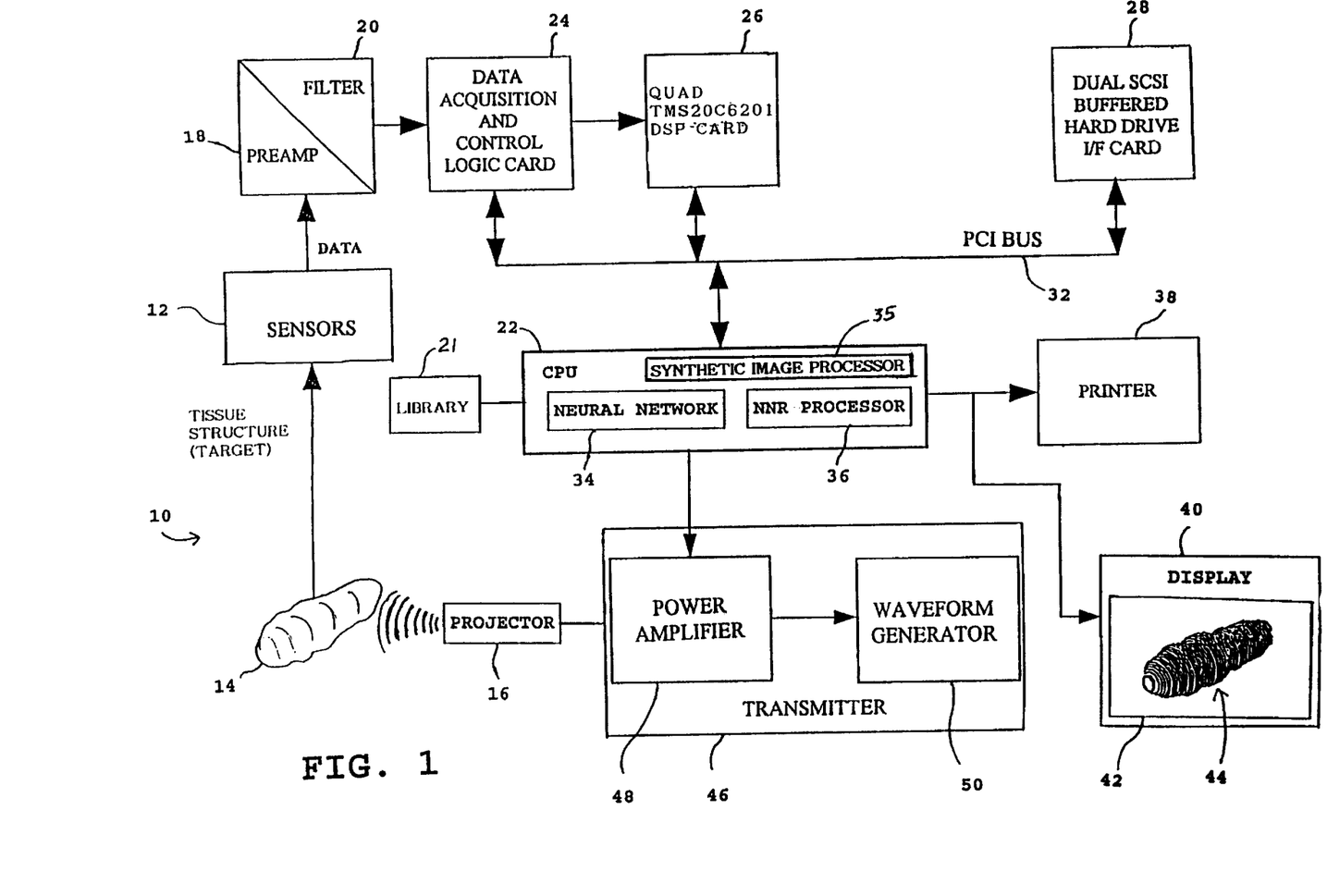
FIG. 1 is a block diagram of the tissue imaging system.

Referring now in specific detail to the drawings, with like reference numerals identifying similar or identical elements, as shown in FIG. 1, the present disclosure describes a tissue imaging system and method for determining the size and shape of biological structures for classification and visualization of normal and abnormal tissues, organs, biological structures, etc.

For clarity of explanation, the illustrative embodiments of the disclosed tissue imaging system and method are presented as having individual functional blocks, which may include functional blocks labelled as "processor" and "processing unit". The functions represented by these blocks may be provided through the use of either shared or dedicated hardware, including, but not limited to, hardware capable of executing software. For example, the functions of the processor and processing unit presented herein may be provided by a shared processor or by a plurality of individual processors. Moreover, the use of the functional blocks with accompanying labels herein is not to be construed to refer exclusively to hardware capable of executing software. Illustrative embodiments may include digital signal processor (DSP) hardware, such as the AT&T DSP16 or DSP32C, read-only memory (ROM) for storing software performing the operations discussed below, and random access memory (RAM) for storing DSP results. Very large scale integration (VLSI) hardware embodiments, as well as custom VLSI circuitry in combination with a general purpose DSP circuit, may also be provided. Any and all of these embodiments may be deemed to fall within the meaning of the labels for the functional blocks as used herein.

In the illustrative embodiment of FIG. 1, the system 10 processes input data signals provided by a plurality of sensors 12 which respond to biological tissue 14 under test in response to low frequency ultrasonic signal insonification; for example, frequencies in the range of about 10 kHz to about 1.0 MHz, with an ultrasonic transmitted waveform produced by a transmitter 46 and an ultrasonic generation device such as a projector 16 both known in the art. The projector 16 is capable of applying a broad range of carefully controlled ultrasound signals from the transmitter 46 to the tissue 14 under test to generate corresponding ramp response signatures. The ramp signatures are detected by the sensors 12 which generate corresponding receive input data signals, which are then analyzed to determine the characteristics of the tissue 14, such as size, shape, composition, volume, and normal or abnormal condition.

The receive input data signals are processed by pre-amplifiers 18 and then filtered by filters 20. The filtered data signals are then processed by a processing unit which includes a central processing unit (CPU) 22 operating in conjunction with a data acquisition and control logic card 24 and a DSP card 26. The CPU 22 and other components of the system 10 may be controlled by an application program written, for example, in the C++ programming language to implement the features and methods described herein.

The memory may be a hard drive 28 and/or RAM, and the optional RAM on the DSP card 26 may be used for faster memory access and processing. The hard drive 28 and cards 24, 26 communicate with the CPU 22 using a bus 32, such as a PCI bus operating the PCI protocol. The CPU 22 may include a neural network 34 and/or a nearest neighbor rule (NNR) processor 36 for classification, as described in greater detail below.

After processing the input data signals, the system 10 generates a processed signal for output by an output device such as a printer 38, or optionally a display 40, an audio system, or other types of output devices known in the art. The output device may output alpha-numeric text messages indicating the condition of the tested tissue 14, and/or may output a classification message indicating the degree to which the tissue 14 under test is within or outside predetermine normal tissue conditions, for example, a percentage compared to 100% normal may be generated and output. The output device may also generate video or graphic representations of the tissue 14 based on the processing of the tissue ramp signatures. For example, the display 40 includes a screen 42 for displaying a graphic representation 44 to a clinician.

The CPU 22 sends control signals to a transmitter 46, including a programmable waveform generator 48 for generating signal waveforms, and including a power amplifier 50 for amplifying such signal waveforms, which are sent to the projector 16 for generating the ultrasound applied to the tissue structure 14.

In an illustrative embodiment, the projector 16 is a piezoceramic projector, comprised of one or more transducer piezoceramic elements, calibrated for insonifying the tissue structure 14, such as the internal organs of a patient, in the frequency range of about 10 kHz to about 100 kHz. The projector 16 may be either the F30 or F41 transducer, available from the Underwater Sound Reference Division (USRD) of the Naval Research Laboratory (NRL). Echo returns from the tissue structures are received by the sensors 12, which may be four calibrated wideband sensors, such as the B&K Model 8103, oriented to provide four distinct target aspects in orthogonal planes.

In an alternative embodiment, the sensors 12 and the projector 16 may be incorporated as a single device, including three custom piezoceramic transducers designed and fabricated to both insonify a tissue structure 14, such as a breast tumor, and receive the backscattered returns in the frequency range of about 100 kHz to about 800 kHz. A class of highly crystalline and oriented thermoplastic polymers, such as polyethylene terephthalate, may also be used for producing a broadband frequency response from about 10 kHz to about 1 MHz. The outputs of the sensors 12 and transducers are sent over coaxial cables to individual pre-amplifiers 18 and anti-aliasing filters 20, and then to a data acquisition card 24 operatively connected to the CPU 22, which may be embodied as a personal computer or a workstation.

The pre-amplifiers 18 may be separate and independent low noise, wideband programmable gain amplifiers, such as the AD 601 which is commonly used in medical ultrasound, preceded by a low noise JFET, to provide an input dynamic range of about 80 dB while minimizing noise and distortion. The pre-amplifiers 18 may be configured on a computer card or board which plugs into the system 10, and which allows the user to change gain settings through software controls without degrading the frequency response as the gain is increased. The filter 20 may be anti-aliasing filters, such as TTE Inc. delay equalized elliptic filters, subsequent to the pre-amplifiers 18 to provide a relatively high rolloff rate of about −84 dB/octave to provide aliasing protection. In the illustrative embodiment, the receiver pre-amplifiers amplifiers 18 have an input dynamic range of about 72 dB, while minimizing noise and distortion.

The output of the anti-aliasing filters 20 is sent to the data acquisition and control logic card 24 or board, which may include, for example, four differential input S/H amplifiers and 12-bit, 10 MHz analog-to-digital converters (ADC), such as the Burr-Brown ADS802 or Analog Devices AD9042, operating as a data acquisition subsystem with a throughput data rate of about 80 Mbytes per second. Each channel of the ADCs may have its own programmable gain amplifier with sufficient gain to provide the full voltage range of the ADC and a common mode rejection ratio of about 100 dB.

The data acquisition subsystem, including the CPU 22, the cards 24–28, and operating and control software, may be incorporated in a "FALCON" computer system, available from Sonoran Microsystems, Inc., or incorporated in an "HT-600" computer system, available from Hi-Techniques, Inc.

The CPU 22 may be an "INTEL"-based "PENTIUM" microprocessor, and the DSP card 26 may be a quad TMS220C6201. The hard drive 28 may include one or more Seagate 18.2 GB fast SCSI hard drives for total storage.

The data acquisition and control logic card 24 formats the data to be in standard personal computer file formats, such as ASCII data formats, to allow the data to be replayed in the laboratory using modified system software and/or using commercial third-party analysis software, such as application programs including S-PLUS or MAPLE. Real-time performance is achieved through the use of multiple COTS DSP boards for the DSP card 26. The DSP card 26 is used to acquire the data, to pack and pass the data to the CPU 22 for storage on the hard drive 28, and to simultaneously band-pass the data, low-pass filter and decimate the band-passed data, and to perform various processing operations such as data normalization, fast Fourier transform (FFT) analysis and parameter estimation.

The system 10 determines a three-dimensional image of biological organs requiring a minimal number of "looks"; for example, at most three slices. The system 10 also generates a diagnostically useful estimate of organ volume and tumor size, and provides an assessment of biological tissue composition by classification of the tissue 14 using the neural network 34 and/or the NNR processor 36. In performing the classification, predetermined 3-D SSI images of normal tissue structures such as biological organs without tumors, as well as estimates of organ volume, are used as the basis of classification, for example, to train the neural network 34 and/or to be processed by the NNR processor 36 to compare the current tissue data with the stored tissue data in the library 21.

The DSP card 26 may use 3-D SSI ultrasound data acquisition, signal processing, and image reconstruction techniques derived from in vivo and in vitro analysis of predetermined and identified tissue to generate the tissue database stored in the hard drive 28.

Synthetic structural imaging (SSI), utilizing the low frequency ramp response signature, offers a unique, effective technique for presenting three-dimensional medical data to the clinician. By applying SSI techniques with advanced signal and image processing methods, the system 10 obtains clinically meaningful measurements of the size and shape of biological organs, as well as their composition and condition.

The system 10 applies low frequency signal insonification (i.e. a ramp signature) matched to the spatial frequencies of the anatomical structure such as tissue 14, in which the lower frequencies provide unique information as to overall dimension and approximate shape of the tissue 14. The system 10 then reconstructs 3-D images of tissue target structures with no more than 3 distinct "looks" or insonifying planes and with a data acquisition time approaching real-time operation.

Estimation of the volume of target tissue, such as organs and tumors, is performed by determining the volume of the target tissue as a unique spatially-invariant classification parameter, derived from processed low frequency echo returns.

In use, the system 10 measures the critical dimensions of various organs, particularly the breast, prostate, uterus, and testes, for the purpose of detecting pathologies in advance of performing a biopsy. The system 10 may also be applied to provide unique anatomical information of the eye, of fetal head growth and heart ventricles, and of tumors and other lesions.

In another embodiment, the system 10 combines SSI techniques using low frequency imaging with known high frequency imaging (for example, using conventional ultrasound frequencies in the 2 MHz to 12 MHz region), so that far fewer imaging planes or "slices" are required to produce meaningful 3-D diagnostic images. In the illustrative embodiment, a maximum of three slices are used as compared to at least 64 slices with previous technology. The unique information provided by SSI, together with reduced data acquisition time, facilitates and significantly improves clinical interpretation for a broad range of tissue studies, particularly in echo-cardiography, in intra-operation procedures, in analyzing specific body organs such as the prostate and kidney, and in ophthalmology.

The ramp response signature is the basis for low frequency characterization, which has the property that the derived physical optics approximation of the target's ramp response R(t) is directly proportional to the target cross-sectional area A(r) along the direction of propagation of the incident field, and may be expressed as:

$$R(t) = \frac{-1}{\pi c^2} A(r) \bigg|_{r=ct/2}$$

in which c is the velocity of propagation in the medium, and r is the radial distance. Thus, the ramp response provides a unique low frequency measure of target shape, orientation and material.

Figure 2:
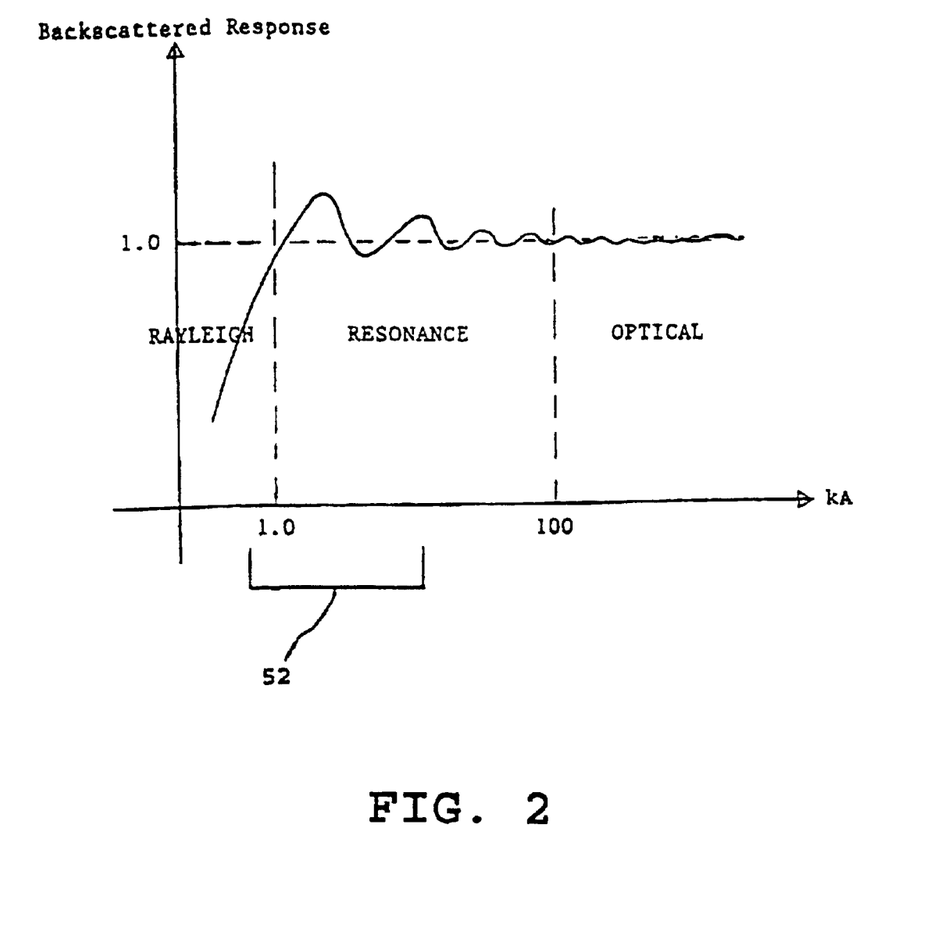
FIG. 2 is a graph of a backscattered response.

The classical acoustic target backscattered response versus ka is shown in FIG. 2 in terms of the Rayleigh, Resonance, and Optical regions, with the ka range depicted for SSI operation, in which k is the frequency wavenumber; i.e. which is $2\pi/\lambda$, $\lambda$ is the wavelength and a is the target radius. From previous experiments with radar and sonar tests, valid estimates of ramp responses may be obtained for the insonification frequencies lying in the upper Rayleigh region and low resonance region of the target's scattering characteristics, i.e. in the region 52 shown in FIG. 2 from about 0.8 ka to about 30 ka. A variety of information may be derived from time and frequency domain analysis of region 52. Using time domain analysis, synthetic image generation as well as the determination of target parameters, such as area, volume, length, diameter, and aspect of the target; i.e. orientation in 3-D space, may be performed. Using frequency domain analysis, feature vectors may be generated such as Doppler characteristics, the aspect of the target, the spectrum shape, and the probability of misclassification. Natural resonances of the target may also be determined from the frequency domain analysis, which facilitate the determination of the type of target, such as liver tissue as opposed to bone tissue.

Low frequency imaging is characterized by a narrow bandwidth and low absorption loss while high frequency imaging is characterized by a wide bandwidth and high absorption loss. Accordingly, high frequency imaging tends to be applied to shorter tissue depths for characterization. The high frequencies characterize the fine detail of the target while the lower frequencies provide information as to overall dimension and approximate shape. Higher frequencies may be used to sharpen the image, but images may be difficult to attain without low frequency information.

In electromagnetic applications, the physical optics approximation provides estimates of the waveform-target size and shape for an illuminated portion of the target, which is significant if the target is a perfect conductor, is smooth, and has dimensions as large as a few wavelengths. Test results show that the ramp response may be approximated by examining a target's electromagnetic response over the frequency range corresponding to wavelengths starting with half the size of the target and increasing to about ten times its dimension.

Ramp responses have also been found to be applicable to ultrasound imaging. The imaging technique used by the system 10 employs low frequency ultrasound signals for target size and shape, and such imaging is enhanced by providing additional information on structural discontinuities utilizing high frequency, short-pulse data.

As shown in FIG. 2, ultrasound having a low frequency ramp response may be applied to the tissue 14. Such ramp responses may be represented by receive echo signals which vary over time, and which may be discontinuous. As described herein, low frequencies may be used for detection and classification of the tissue 14. Although there may be a many-to-one correspondence between a ramp response feature and the possible structural discontinuities that may produce it, this ambiguity may be resolved by employing short, high frequency pulses using the impulse response. Accordingly, the ramp response from a low frequency pulse may be distinguished by using high frequencies short pulses. The target impulse response is sensitive to the curvature in the cross-sectional area and thus sensitive to boundary discontinuities and scattering centers. Therefore, by including high frequencies to define target scattering centers, the number of low frequencies required to image the target may be significantly reduced. This suggests that the optimum target response is a weighted sum of the ramp, step, and impulse responses.

In another embodiment, the low frequencies which generate the ramp response are used as a feature vector for pattern classification by the neural network 34 and/or the nearest neighbor rule (NNR) processor 36. As inputs to the neural network 34, the ramp responses may be processed as an input feature vector to generate a neural network output which classifies the ramp response relative to a training set of tissue data. The nearest neighbor rule, as implemented by the NNR processor 36, is generally a robust decision rule ideally suited for discriminating low frequency data. Radar test results have shown that over 90% reliability of classification may be achieved with about four frequencies of the ramp response, utilizing amplitude information and vertical polarization data; fewer frequencies are needed by employing phase information, since phase is a sensitive measure of changes in target shape. In acoustic applications, since the particle velocity is "rotational", only amplitude and phase modulation data is required.

Heretofore, low frequency insonification has not been widely used for biological analysis and diagnosis. One low frequency diagnosis technique using frequencies in the range of about 10 Hz to about 1000 Hz is capable of imaging abnormal regional elasticity in tissue, referred to as sonoelasticity, by mechanically vibrating tissue at low frequency which modulates an ultrasound carrier frequency. The resulting Doppler displacements are a function of tissue stiffness; i.e. Young's modulus, and may then be displayed with a Doppler flow mapping imaging system, including color flow mapping, known in the art.

Preliminary indications are that "stiff" or "hard" tissue vibrates less than soft tissue, depending upon the degree of hardness, and that vibrational frequencies between about 100 Hz and about 300 Hz are useful for discrimination.

The low frequencies required for applying SSI techniques are generally higher than that used for sonoelasticity or elastography. SSI provides estimates of classification parameters which have not heretofore been derivable otherwise, which, in turn, are used by the system 10 to derive feature patterns describing benign and malignant disease.

The acoustic echo signature is generally rich with information from distributed tissue structures, and by using SSI techniques for acoustic and elastic scattering in real biological media, such tissue structures may be detected and classified with substantial accuracy.

The system processing takes into consideration the frequency dependence of tissue attenuation, the response of tissue shear wave generation, and the impact of interconnective tissue and adjacent structures, veins and arteries, as well as the effect of wide-beam insonification.

Ultrasound attenuation increases with increasing frequency and the depth of tissue penetration. For significant variance in response due to attenuation relative to the total dynamic range of the ramp response, the variance affects the relationship between the ramp response and organ geometry. The frequency range required for applying SSI to tissue organs of interest is about 10 kHz to about 100 kHz. For one-way longitudinal absorption of about 1.0 dB/cm-MHz, the two-way absorption incurred at a depth of about 10 cm is about 0.2 dB to about 2.0 dB over the frequency band.

Such a variance may be compensated in the transmitted ultrasound signal by having a dynamic range of about 48 dB. Based on the dimensions of actual human tissue organs considered, the SSI frequencies employed may also generate vibrational shear modes. In practice, some cross-coupling of modes between shear and compression may occur, so the system 10 evaluates such shear waves. Typically, the shear wave attenuation coefficient has been measured to be about $10^4$ times the longitudinal wave attenuation coefficient.

Theoretically, the biological ultrasound ramp response is affected by tissue/organ attachments such as blood vessels, cartilage and neighboring anatomical structures. However, at the spatial frequencies required for the synthetic structural imaging of much larger organs, the associated vessels are generally acoustically transparent.

Since normal SSI operation employs a wide beamwidth, several organs may be insonified at one time. In order to resolve the echo ramp signature into components related to individual organs, the system 10 uses a priori information concerning the general spatial properties of the organs, a selection of the aspect of the target, and time gating. High frequency 2-D image data may be used to resolve any ambiguities in identification and classification. The system 10 is then capable of obtaining the size and shape of biological organs and tumors, and determining their composition.

Prior to use, the system 10 is configured to use in vivo and in vitro measurements of the low frequency ramp response of tissue, including organs and tissue-mimicking breast tumors, to derive empirical 3-D images and measures of volume and material composition, which are stored in a library database 21 and may be located in the hard drive 28. Such data from tissue organs may be naturally corrupted by tissue speckle, system noise, and artifacts, which may be introduced by tissue/organ attachments and adjacent structures. The system 10 may be integrated into known imaging systems and used to conduct in vivo tests of human subjects to enhance and refine the library database 21.

The system 10 uses the transmitted signals from the projector 16: for empirically obtaining the ramp response of specific biological organs and tumors; for generating low frequency synthetic images of biological organs and tumors; for estimating the volume of the organs and tumors; for deriving measures of tissue composition from the measured ramp response, such as density and elasticity; for assessing other SSI biological structural characteristics, such as attenuation and target aspect; and for assessing the effects of shear waves and wide-beam insonification.

From the empirical data collection, unique signal waveforms or ultrasonic signatures are stored in the hard drive 28 corresponding to specific tissue organs and tumors of interest. The signal waveforms are designed such that, when transmitted, the signal waveform generates the tissue phantoms with a distinct ramp response signature for specific tissue organs, such as prostate, kidney, eye, and breast tumors. The signal waveform, including both amplitude and phase modulation over the required frequency band, may be adjusted to match the spatial frequencies characterizing these structures.

For example, the system 10 may use signal waveforms with frequencies from about 10 kHz to about 100 kHz for organ visualization, and frequencies from about 100 kHz to about 800 kHz for visualizing breast tumors from about 2 mm to about 5 mm in size. For such organ detection and identification, the transmitted signal fundamental-to-harmonic ratio is about 48 dB, and the signals used may be transmitted according to a predetermined complex function to provide sufficient dynamic range and minimal false echoes.

Prior to collecting data, all system components are calibrated to establish, for example, the ultrasonic spatial and frequency responses, including projector and hydrophonic spatial characteristics and responses; source level and spectral purity; receiver bandwidths; the gain of the pre-amplifier 18 and input noise level; any integral and differential non-linearities; any harmonic and IM distortion; any spurious-free dynamic range of the ADCs; any back-scatter data; and any background transients naturally-occurring within the measured frequency band. The amplitude and phase differential between channels may then be measured and compensated. In the system 10, the power levels employed for transmission may be compatible with SPTA requirements specified in AIUM/NEMA Standard 9-17-1981.

The DSP card 26 performs echo data processing in which an FFT of the target's complex spectral response is appropriately weighted to construct an FFT approximation of the target's ramp response signature. The ramp response derived from the echo amplitude and phase data is further processed in order to approximate the target cross-sectional area function or "profile function". The empirically-derived profile functions are modified based upon known geometrical constraints and are used as the input data for the image reconstruction techniques employed by the CPU 22.

Image reconstruction may use, for example, limiting-surfaces to generate an isometric image of the target, in which the target generally includes a few simple shapes, such as shapes described by a circular or elliptical cross-section. Image reconstruction of such shapes generally requires few parameters for contour estimation. A generalized surface, such as an ellipse, is fitted to the set of profile functions, in which at least one such generalized surface is calculated for each look angle. An image is then generated by calculating an image surface which encloses a volume common to substantially all of the single-aspect angle limiting surfaces. Orthogonality between the look angles may be used to greatly simplify such image processing.

The three-dimensional reconstructed images are compared with gross examination of actual tissue images in the library. The actual volume of each tissue phantom employed is compared with the volume measured by integrating the empirically-derived profile functions at the various aspects. The volume error is used as a measure of image accuracy. In addition, the ramp response is examined to derive information concerning the composition of the tissue.

Figure 3:
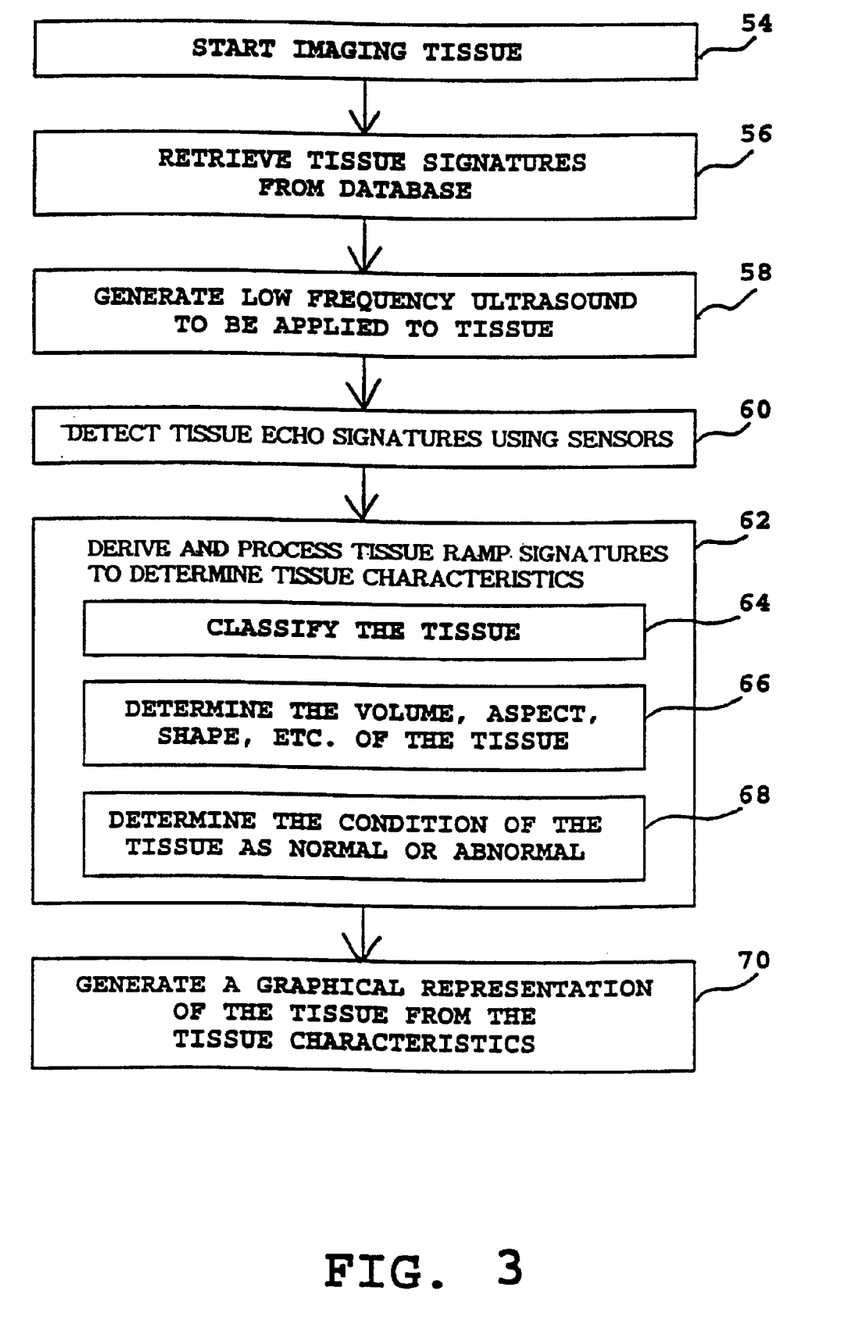
FIG. 3 is a flowchart of the method of operation of the tissue imaging system.

As shown in FIG. 3, the system 10 operates using a method including the steps of: starting the imaging of the tissue 14 in step 54 by, for example, initializing and calibrating the system 10; retrieving tissue signatures from the database in the hard drive 28 in step 56; generating low frequency ultrasound in step 58 using the tissue signatures to be applied to the tissue 14; detecting tissue structures in step 60 using the sensors 12, with the tissue ramp signatures being generated by the tissue 14 in response to the low frequency ultrasound; and processing the tissue ramp signatures to determine tissue characteristics in step 62.

The step 62 of processing the tissue ramp signatures may include, for example, any combination of steps 64–68. In an illustrative embodiment, the system 10 classifies the tissue 14 in step 64 using a classifier such as the neural network 34 and/or the NNR processor 36 which uses predetermined tissue data for classifying the tissue 14. A discussion of neural networks and NNR processors is found in U.S. patent application Ser. No. 09/167,868, the contents of which are incorporated herein by reference.

In addition, the system 10 determines the volume, aspect, shape, etc. of the tissue 14 in step 66 using SSI techniques, signal processing techniques such as FFT processing, etc., and the system 10 also determines a condition of the tissue 14 in step 68 as being normal or abnormal.

The system 10 may then output the tissue characteristics to a clinician. The system 10 may also use such tissue characteristics to generate a graphic representation 44 of the tissue 14 in step 70.

Using the system 10 and methods described herein, a clinician may then non-invasively, acoustically measure and generate an image of tissue structures in a patient to provide unique information concerning the size and shape of biological structures for classification and visualization of normal and abnormal tissues, organs, biological structures, etc. with improved accuracy and diagnostic analysis.

While the disclosed tissue imaging system and method have been particularly shown and described with reference to the preferred embodiments, it is understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. An acoustic measurement and imaging system comprising:
 a projector for generating low frequency ultrasound signals in a frequency range from about 10 kHz to about 1 MHz in a target tissue structure;
 a sensor in communication with the projector for receiving tissue echo signatures generated by the interaction of said target tissue structure with the low frequency ultrasound signals;
 a central processor in communication with the receiver to determine a low frequency ramp response from said tissue echo signatures;
 memory graphics for generating a graphic representation of the target tissue structure from the low frequency ramp response using an acoustic database of stored tissue data.

2. An acoustic measurement and imaging system as in claim 1, further comprising a classifier in communication with said memory graphics to classify the target tissue as to type or condition of the target tissue using said database of stored tissue data.

3. An acoustic measurement and imaging system as in claim 2, wherein the classifier includes a neural network.

4. An acoustic measurement and imaging system as in claim 2, wherein the classifier includes a nearest neighbor rule processor.

5. An acoustic measurement and imaging system as in claim 2, wherein the classifier includes a neural network, driven by a feature vector comprising a target profile function.

6. An acoustic measurement and imaging system as in claim 5, wherein the feature vector further comprises one or more of (a) a target parameter estimate, comprising one or more of aspect, volume, length, diameter, area, and speed; (b) one or more measures of tissue composition, comprising one or more of density and elasticity; and (c) probability of misclassification as components.

7. An acoustic measurement and imaging system as in claim 2, wherein the classifier includes a nearest neighbor rule processor, driven by a feature vector containing the target profile function.

8. An acoustic measurement and imaging system as in claim 7, wherein the feature vector further comprises one or more of (a) a target parameter estimate, comprising one or more of aspect, volume, length, diameter, area, and speed; (b) one or more measures of tissue composition, comprising one or more of density and elasticity; and (c) probability of misclassification as components.

9. An acoustic measurement and imaging system as in claim 1, wherein said acoustic database of stored tissue data includes amplitude and phase information as a function of tissue type, tissue dimensions, target direction and insonified frequency.

10. An acoustic measurement and imaging system comprising:
 a projector for generating low frequency ultrasound signals in a frequency range from about 10 kHz to about 1 MHz to target tissue to generate corresponding tissue echo signatures;
 at least one sensor for detecting said tissue echo signatures from the target tissue and for generating corresponding input data signals;
 at least one preamplifier for signal conditioning the input data signals;
 at least one filter for processing the input data signals;
 a central processor for processing the filtered input data signals based on a set of stored tissue acoustic data and generating at least one output signal; and
 graphics structure for generating a graphic representation of the properties of the target tissue from at least one output signal.

11. An acoustic measurement and imaging system as in claim 10 wherein the central processor comprises a digital signal processor and a CPU, and operates in conjunction with data acquisition and control logic circuitry and a memory unit.

12. An acoustic measurement and imaging system as in claim 10, wherein the central processor includes a neural network.

13. An acoustic measurement and imaging system as in claim 10, wherein the central processor includes a nearest neighbor rule processor.

14. An acoustic measurement and imaging system as in claim 10, wherein the graphics structure includes a printer.

15. An acoustic measurement and imaging system as in claim 10, wherein the graphics structure includes a video display.

16. An acoustic measurement and imaging system as in claim 10, comprising three or four calibrated sensors oriented to provide three or four distinct target aspects.

17. An acoustic measurement and imaging system as in claim 10, wherein the projector and plurality of sensors are configured as a single unit including at least two piezoceramic transducers designed to insonify target tissue and receive backscatter returns.

18. An acoustic measurement and imaging system as in claim 17, wherein the backscatter returns are in the frequency range from about 0.8 ka to about 30 ka, where k is the frequency wavenumber, $2\pi/\lambda$, $\lambda$ is the wavelength, and a is the target dimension.

19. An acoustic measurement and imaging system as in claim 10, wherein the preamplifier is a low noise, wideband programmable gain amplifier.

20. An acoustic measurement and imaging system as in claim 10, wherein the graphics structure includes a printer connected to the central processor and is responsive to the reconstructed image data developed by the central processor corresponding to a ramp profile function of a three-dimensional tissue target.

21. An acoustic measurement and imaging system as in claim 10, wherein the graphics structure includes a video display connected to the central processor and is responsive to the reconstructed image data developed by the central processor corresponding to a ramp profile function of a three-dimensional tissue target.

22. An acoustic measurement and imaging system as in claim 10, wherein the backscatter returns are preferably in the frequency range from about 0.5 ka to about 10 ka, where k is the frequency wavenumber, $2\pi/\lambda$, $\lambda$ is the wavelength, and a is the target dimension.

23. An acoustic measurement and imaging system as in claim 10, wherein the preamplifier is a low noise, wideband programmable gain amplifier, compensating in part for the attenuation incurred as a function of frequency and depth of tissue penetration.

24. A method for acoustic measurement and imaging of target tissue comprising the steps of:

providing an acoustic measurement and imaging system comprising a projector for generating low frequency ultrasound in target tissue, at least one sensor in communication with the projector for receiving tissue echo signatures generated by the interaction of said target tissue structure with low frequency ultrasound signals from said projector, a central processor in communication with the receiver to determine a low frequency ramp response from said tissue echo signatures, and memory graphics for generating a graphic representation of the target tissue from the low frequency ramp response using an acoustic database of stored tissue data;

initializing and calibrating the acoustic measurement and imaging system;

retrieving tissue echo signatures from the acoustic database;

generating low frequency ultrasound to the target tissue;

detecting tissue echo signatures using the at least one sensor; and processing the tissue echo signatures to determine tissue characteristics of the target tissue.

25. A method for acoustic measurement and imaging of target tissue as in claim 24, further comprising the step of determining one or more of volume, aspect and shape of the target tissue.

26. A method for acoustic measurement and imaging of target tissue as in claim 24, further comprising the step of generating a graphic representation of at least a portion of the target tissue structure.

27. A method for acoustic measurement and imaging of target tissue as in claim 24, wherein the step of processing the tissue echo signatures includes the step of classifying the tissue using a neural network using predetermined tissue data.

28. An acoustic measurement and imaging system comprising:

at least one projector for generating low frequency ultrasound signals in target tissue structure;

at least one sensor in communication with the projector for receiving tissue echo signatures from various target directions or aspect angles generated by the interaction of said target tissue structure with the low frequency ultrasound signals:

a central processor in communication with the receiver to compute the target ramp response from said low frequency tissue echo signatures;

memory graphics for storing a three-dimensional representation of the target tissue structure from the target ramp response and storing estimated target property values, using an acoustic database of stored tissue data; and whereby the target's echo signature is used to compute the physical optics approximation of the target's ramp response, which is directly proportional to the target cross-sectional area (profile) function along the direction of propagation of the incident acoustic field and a volume estimate obtained from the integral of the profile function, with both metrics used as the input data for target image reconstruction and target classification by the central processor.

* * * * *